United States Patent [19]

Chance et al.

[11] 4,006,203
[45] Feb. 1, 1977

[54] PHOSPHINYL GUANIDINE DERIVATIVES

[75] Inventors: Leon H. Chance, New Orleans; Cletus E. Morris, Metairie, both of La.

[73] Assignee: The United States of America as represented by the Secretary of Agriculture, Washington, D.C.

[22] Filed: Mar. 15, 1976

[21] Appl. No.: 667,054

[52] U.S. Cl. ............................ 260/940; 260/551 P; 260/944

[51] Int. Cl.² .......................................... C07F 9/24

[58] Field of Search ................ 260/940, 944, 551 P

[56] References Cited

OTHER PUBLICATIONS

Beyer et al., J. Prakt. Chem., 16, 132 (1962).
Cates et al., J. Pharm. Sci., 55, 966, (1966).
Cramer et al., Chem. Ber., 91, 911, (1958).

*Primary Examiner*—Richard L. Raymond
*Attorney, Agent, or Firm*—M. Howard Silverstein; David G. McConell; Salvador J. Cangemi

[57] ABSTRACT

The following new compounds were prepared from cyanoguanidine or guanylurea as potential flame retardants for cellulosic textiles -2-cyano-1-[bis-(dimethylamino)phosphinyl]guanidine, 2-cyano-1-(diethoxyphosphinyl)guanidine, and 2-carbamoyl-1-(diethoxyphosphinyl) guanidine. The successful phosphorylation of guanylurea required use of a dry, aprotic solvent.

3 Claims, No Drawings

PHOSPHINYL GUANIDINE DERIVATIVES

This invention relates to some novel phosphiny-derivatives and to the preparation thereof.

The main object of the instant invention is to provide phosphinylguanidine compounds which are useful in flame retardant compositions for cellulosic materials such as cotton and rayon.

A second object of the instant invention is to provide methods of preparing new phosphinylguanidine derivatives.

In the course of investigating compounds containing phosphorus and nitrogen as possible flame retardants for textiles, we prepared new compounds Ia-c from cyanoguanidine or guanylurea:

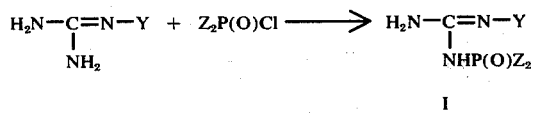

| | | |
|---|---|---|
| Ia | Y = CN | Z = NMe$_2$ |
| Ib | Y = CN | Z = OEt |
| Ic | Y = C(O)NH$_2$, | Z = OEt |

A search of the literature for compounds with structure I, where Y = CN or C(O)NH$_2$ and Z is alkoxy or aryloxy, revealed that only three such cyanoguanidine derivatives (Y = CN) and one such guanylurea derivative (Y = C(O)NH$_2$) have been reported, all of them containing aryloxy groups. [Beyer, H., Pyl, T., and Lemke, H., J. Prakt. Chem. 16, 132 (1962)]. Only three such aliphatic derivatives of guanidine itself (Y = H) have been reported. [Cates, L. A., Ferguson, N. M., J. Pharm. Sci. 55, 966 (1966), and Cramer, F., Vollmar, A., Chem. Ber. 91, 911 (1958)]. No references to diaminophosphinyl derivatives of guanidine, cyanoguanidine, or guanylurea (I, Y = H, CN, or (C(O)NH$_2$; Z = NH$_2$ or NR$_2$) could be found in the literature.

Beyer et al. prepared 2-cyano-1-(diaryloxyphosphinyl)guanidines by adding the diaryl phosphorochloridate to a solution of 1 mole of cyanoguanidine and 2 moles of sodium hydroxide in aqueous acetone. We used this procedure to prepare Ia and Ib, but no such phosphorylations or ganylurea have been reported. The 2-carbamoyl-1-(diaryloxyphosphinyl)-guanidine reported by Beyer et al. was prepared by hydrolysis of the corresponding cyanoguanidine. Our attempts to prepare Ic from diethyl phosphorochloridate and guanylurea in methanol or in a benzene-water mixture gave products from which only guanylurea salts could be isolated. The desired product was obtained when a suspension of guanylurea in an aprotic solvent was used in the reaction. Ic was isolated in 13% yield when acetonitrile was used, and in 46% yield when dry acetone was used with precautions to exclude moisture from the system. The higher yield in the latter case was probably due to absence of moisture rather than to choice of solvent.

We also prepared Ic by the hydrolysis of the corresponding cyanoguanidine, Ib.

It is obvious in the general formula Z$_2$P(O)Cl that Z may be NEt$_2$, NPr$_2$, etc., or OMe, OPr, etc., in addition to NMe$_2$ and OEt used in the preparation of Ia and Ic as described in this invention.

In addition to being useful in flame retardant compositions for cellulosic materials, compounds Ia, Ib, and Ic of this invention are useful in the synthesis of other compounds. For example, Ib was used in the synthesis of Ic as previously stated.

The compounds of this invention were identified by elemental analyses and infrared absorption spectra.

The invention will be more clearly understood by the following illustrative examples.

EXAMPLE 1

2-Cyano-1-[bis(dimethylamino)phosphinyl]guanidine Ia.

A solution of 17.1 grams (0.100 mole) of tetramethylphosphorodiamidic chloride (5) in 10 ml of dry acetone was added dropwise at 25°–29° C during 32 min to a stirred solution of 8.4 grams (0.100 mole) of cyanoguanidine and 15.8 grams (0.200 mole) of 50.5% aqueous sodium hydroxide in a mixture of 50 ml of acetone and 40 ml of water. The mixture was stirred for 1 hr longer, then acidified by addition of 6.0 grams (0.100 mole) of glacial acetic acid. Addition of a little more acetone induced crystallization. The mixture was cooled and filtered to obtain 4.3 grams (20%) of crystals. Recrystallization from ethanol gave colorless crystals; mp 213° C (with gas evolution).

Ia is soluble in hot water, slightly soluble in hot ethanol, and practically insoluble in 2-propanol, acetone, acetonitrile, and chloroform. The ir spectrum showed absorption bands at 2192(s, C=N), 1630(s, NH$_2$), 1304(s, CH$_3$), 1200(s, P=O), 1170(s, CH$_3$), and 1064(s, PNC) cm$^{-1}$. Anal. Calcd. for C$_6$H$_{15}$N$_6$OP : C, 33.03; H, 6.93; N, 38.52; P, 14.20. Found: C, 33.16; H, 7.10; N, 38.68; P, 14.19.

EXAMPLE 2

2-Cyano-1-(diethoxyphosphinyl)guanidine (Ib)

A solution of 17.29 grams (0.100 mole) of diethyl phosphorochloridate in 10 ml of acetone was added dropwise during 37 min to a stirred solution of 8.41 grams (0.100 mole) of cyanoguanidine and 15.69 grams (0.200 mole) of 51% aqueous sodium hydroxide in 42 ml of water and 50 ml of acetone. During the addition the temperature rose to 47° C and the two liquid phases initially present coalesced. The solution was stirred for 30 min longer and poured into 300 ml of water. Acidification with 17.73 grams (0.106 mole) of 36% acetic acid did not lead to separation of a product. The solution was evaporated in a stream of air until crystallization was observed, then chilled and filtered to obtain 6.54 grams (29.7%) of crystals; mp 164°–165.5° C. The product was recrystallized from acetone: mp 164°–165° C.

Ib is soluble in ethanol, 2-ethoxyethanol, hot water, hot 2-propanol, hot acetone, and hot acetonitrile, and practically insoluble in chloroform. The ir spectrum showed absorption bands at 2214(s, C=N, 1662(s, NH$_2$), 1243(s, P=O), 1160(w, POEt), 1044(vs, POC) cm$^{-1}$.

Anal. Calcd. for C$_6$H$_{13}$N$_4$O$_3$P: C, 32.73; H, 5.95; N, 25.45; P, 14.07. Found: C, 32.77; H, 5.96; N, 25.50; P, 14.06.

EXAMPLE 3

Reaction of Diethyl Phosphorochloridate with Guanylurea in Methanol.

A solution of 1.08 grams (0.0200 mole) of sodium methoxide in 10 ml of methanol was added to a suspension of 3.02 grams (0.0100 mole) of guanylurea sulfate in 35 ml of methanol. The mixture was stirred for 2 hr, heated to boiling, allowed to cool to 45° C, and filtered to remove sodium sulfate.

Triethylamine (2.09 grams, 0.0207 mole) was added to the guanylurea solution, then a solution of 3.47 grams (0.0201 mole) of diethyl phosphorochloridate in 5 ml of acetone was added dropwise during 5 min as the temperature rose to 41° C. The mixture was stirred 30 min and allowed to stand overnight. Solvent was removed on a rotary evaporator and the residue was washed twice with chloroform to remove triethylamine hydrochloride. This left 1.94 grams (70%) of guanylurea hydrochloride, which was recrystallized from ethanol and identified by elemental analyses, ir, and qualitative tests for guanylurea (Ni complex formation) and chloride ion. Since this method was not successful the following method was used.

2-Carbamoyl-1-(diethoxyphosphinyl)guanidine (Ic)

A. From Guanylurea — A solution of guanylurea in methanol was prepared essentially as described above and solvent was removed on a rotary evaporator. Recrystallization of the residue from ethanol gave guanylurea in 75% yield.

Under a nitrogen atmosphere 5.64 grams (0.0552 mole) of guanylurea, 85 ml of dry acetone, and 5.97 grams (0.0552 mole) of guanylurea, 85 ml of dry acetone, and 5.97 grams (0.0590 mole) of triethylamine were placed in a 200-ml flask equipped with a mechanical stirrer, a thermometer, a dropping funnel, a nitrogen inlet, and a drying tube. A solution of 9.53 grams (0.0552 mole) of diethyl phosphorochloridate in 10 ml of acetone was added dropwise to the stirred suspension during 13 min. The flask was cooled intermittently in an ice bath to hold the temperature at 27°–30° C. The suspension was stirred for 2 hr longer, allowed to stand overnight, and filtered. The residue was washed with acetone and recrystallized from chloroform to obtain 2.61 grams of crystals; mp 164°–165° C (cloudy melt). More Ic was isolated from the mother liquor and the acetone solution; the total yield of material with mp above 164° was 6.08 grams (46.2%). The mp of Ic prepared from granylurea was not depressed on mixture with Ic prepared by hydrolysis of Ib.

B. From Ib — A mixture of 4.40 grams (0.0200 mole) of Ib, 1.91 grams of 38% hydrochloric acid, and 60 ml of ethanol was stirred and heated under reflux for 30 min, then evaporated overnight in a stream of air. The residual paste was stirred with acetone and filtered. The unidentified acetone-insoluble material, mp 257°–260° C, weighed 0.18 gram. The acetone solution was evaporated, water was added, and the resulting crystals were collected and recrystallized from methanol to obtain 0.30 gram (7%) of Ib, mp 161°–163° C. Crystals obtained from the two mother liquors were combined and recrystallized from water and from acetone to obtain 0.28 gram (6%) of Ic; mp 164.5°–165° C (cloudy melt, solidifying at higher temperatures and remelting near 245° C). The analytical sample was recrystallized from acetone: mp 170°–170.5° C (cloudy melt).

Increasing the reaction time to 3 hr did not increase the amount of Ic isolated, but in this case no Ib was recovered. The unidentified acetone-insoluble product was again isolated in low yield.

Ic is soluble in 2-ethoxyethanol, warm ethanol, hot water, and hot 2-propanol, slightly soluble in hot acetone and hot acetonitrile, and practically insoluble in chloroform. The ir spectrum showed absorption bands at 3406(s, NH), 3315(m, NH), 1202(s, P=O), 1165(w, POEt), 1024(s, POC)cm$^{-1}$.

Anal. Calcd. for $C_6H_{15}N_4O_4P$: C, 30.26; H, 6.35; N, 23.52; P, 13.00. Found: C, 30.43; H, 6.40; N, 23.60; P, 13.16.

EXAMPLE 4

Cotton Fabric Treatment

Dimethylformamide (DMF) solutions of compounds 1a, 1b, and 1c in Examples 1, 2, and 3 were prepared in concentrations of 10%, 20%, and 20% (by weight), respectively. It was necessary to warm the DMF to dissolve 1a. Samples of cotton flannelete were impregnated with each solution, and each sample was dried for 5 minutes at 85° C. The samples treated with 1a, 1b, and 1c had Strip Flame Test angles for flame retardancy of 90°, 135°, and 135°, respectively. An angle of 90° indicates fair flame-retardancy, and 135° indicates good flame-retardancy. The Strip Flame Test was performed by the method of W. A. Reeves, et al., Textile Research Journal 23, 527 (1953).

We claim:
1. 2-Cyano-1-[bis(dimethylamino)phosphinyl]guanidine.
2. 2-Cyano-1-(diethoxyphosphinyl)guanidine.
3. 2-Carbamoyl-1-(diethoxyphosphinyl)guanidine.

* * * * *